United States Patent
Grudzinski et al.

(10) Patent No.: US 10,007,961 B2
(45) Date of Patent: Jun. 26, 2018

(54) TREATMENT PLANNING SYSTEM FOR RADIOPHARMACEUTICALS

(75) Inventors: Joseph J. Grudzinski, Madison, WI (US); Robert Jeraj, Madison, WI (US); Wolfgang A. Tome, Madison, WI (US); Jamey P. Weichert, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 866 days.

(21) Appl. No.: 12/556,323

(22) Filed: Sep. 9, 2009

(65) Prior Publication Data
US 2011/0060602 A1 Mar. 10, 2011

(51) Int. Cl.
*G06Q 50/22* (2018.01)
*G06F 19/00* (2018.01)

(52) U.S. Cl.
CPC ............. *G06Q 50/22* (2013.01); *G06F 19/00* (2013.01)

(58) Field of Classification Search
CPC ......... A61K 2300/00; A61K 2039/545; G06Q 50/22
USPC ...................................... 705/2–4; 378/65, 96
See application file for complete search history.

(56) References Cited

U.S. PATENT DOCUMENTS

| | | | |
|---|---|---|---|
| 7,481,758 B2* | 1/2009 | Weil et al. | 600/2 |
| 7,668,662 B2* | 2/2010 | Kroll et al. | 702/19 |
| 7,872,235 B2* | 1/2011 | Rousso et al. | 250/363.04 |
| 8,660,800 B2* | 2/2014 | Von Busch et al. | 702/19 |
| 2005/0196339 A1 | 9/2005 | Weichert et al. | |
| 2006/0173725 A1* | 8/2006 | Abraham et al. | 705/8 |
| 2008/0214933 A1* | 9/2008 | Von Busch et al. | 600/431 |
| 2009/0175418 A1* | 7/2009 | Sakurai et al. | 378/98.5 |
| 2009/0304582 A1* | 12/2009 | Rousso et al. | 424/1.61 |
| 2011/0178359 A1* | 7/2011 | Hirschman et al. | 600/4 |

FOREIGN PATENT DOCUMENTS

WO 2009031073 A2 12/2009

OTHER PUBLICATIONS

Wahl, "Preclinical and Clinical Evaluation of Novel Agents for Noninvasive Imaging of Prostate Cancer." Aug. 1999: 16.*

* cited by examiner

*Primary Examiner* — Mark Holcomb
(74) *Attorney, Agent, or Firm* — Boyle Fredrickson, SC

(57) ABSTRACT

A treatment schedule for radiopharmaceuticals is developed by collecting a volumetric history of tissue uptake in identified volumes of interest using emitted-radiation scans and relating this data to a treatment-radiopharmaceutical to develop a quantitatively accurate radiation treatment schedule of delivery amounts and delivery times of the treatment-radiopharmaceutical. This data may also be used to model biological effective dose and to prepare augmenting external radiation beam treatment schedules.

22 Claims, 3 Drawing Sheets

TREATMENT PLANNING SYSTEM FOR RADIOPHARMACEUTICALS

STATEMENT REGARDING FEDERALLY SPONSORED RESEARCH OR DEVELOPMENT

This invention was made with United States government support awarded by the following agency:

NIH CA014520, CA109656

The United States government has certain rights in this invention.

BACKGROUND OF THE INVENTION

The invention relates generally to methods and apparatus for the treatment of tumors using radiopharmaceuticals and, in particular, to a system for the computerized scheduling of the administration of such radiopharmaceuticals.

Radiopharmaceuticals include materials that may "target" specific tissues to deliver radioactive materials to those targeted tissues. Such radiopharmaceuticals generally combine a radioactive component such as a radionuclide with a tracer component exhibiting selective uptake in target tissue. Such radiopharmaceuticals allow imaging or treatment of specific tissues in the body after a generalized introduction of the radiopharmaceutical to the body, for example, by injection into the bloodstream.

When such radiopharmaceuticals are used for radiation therapy, the quantity and timing of the administration of the radiopharmaceutical must provide a radiation dose to the tissue sufficient to kill tumor cells and the radiation dose must be sustained for a time period related to the reproduction rate of tumor cells. While the selective uptake of radiopharmaceuticals may concentrate the radioactive component in the target tissue, the selectivity of such mechanisms is not perfect and accordingly the quantity and timing of the administration of the radiopharmaceuticals must also be limited to reduce toxicity to healthy-tissues that exhibit some uptake of the radiopharmaceutical.

Selecting the appropriate quantity and timing for administration of a radiopharmaceutical may be approximated by using a model of a "standard man" or extrapolation from animal models such as rodents to humans. Differences between animals and humans and even among humans make such determinations imprecise at best.

SUMMARY OF THE INVENTION

The present invention provides a system for precisely tailoring the quantity and timing of the administration of a radiopharmaceutical to a particular patient. In one embodiment, the invention takes advantage of an analogous biological behavior between certain imaging and therapeutic radiopharmaceuticals. The imaging-radiopharmaceutical may be used to prepare "time activity curves" describing the uptake of the radiopharmaceutical in different designated volumes of interest using SPECT, PET or similar imaging modalities. The volumes of interest may be selected to include a target tissue and sensitive healthy-tissue. The collected time activity curves then form the basis for a model indicating uptake of a treatment-radiopharmaceutical. This model yields a precise, patient-specific treatment schedule for administering the radiopharmaceutical accommodating constraints such as minimum radiation dose-rate and healthy-tissue toxicity. This two-step technique can provide sufficient precision to make practical the combination of radiopharmaceutical treatment with other radiation treatment techniques such as external-beam radiotherapy.

Specifically then, the present invention permits the development of a treatment schedule for a treatment-radiopharmaceutical by using a three-dimensional data set recording a history of tissue uptake of an imaging-radiopharmaceutical in at least one volume of interest. This history of tissue (such as a time activity curve or TAC) shows the time during which the imaging-radiopharmaceutical is active in the volume of interest and may be used to prepare a treatment schedule for the treatment-radiopharmaceutical, the latter having similar uptake characteristics as the imaging-radiopharmaceutical. The treatment schedule provides a set of pharmaceutical delivery amounts and delivery times for the treatment-radiopharmaceutical.

It is thus a feature of at least one embodiment of the invention to employ current imaging technologies to provide quantitative guidance for therapeutic radiopharmaceuticals tailored for an individual patient.

The system may receive a desired treatment radiation dose-rate and the treatment schedule may determine radiopharmaceutical delivery amounts and delivery times to provide the desired treatment radiation dose-rate in the volume of interest.

It is thus a feature of at least one embodiment of the invention to use radiopharmaceutical imaging systems to develop an uptake model for that patient that may then be manipulated to produce an accurate treatment schedule.

In one embodiment, the invention deduces an active time of the imaging-radiopharmaceutical in at least two volumes of interest and the desired treatment radiation dose-rate is received for a first volume of interest and a toxicity limit is received for the second volume of interest. The delivery amount and delivery time of the treatment schedule is calculated to maximize a time period when the radiation dose-rate in the first volume of interest is no less than the desired treatment radiation dose-rate under the condition that the radiation dose-rate in the second volume of interest be no greater than the toxicity limit.

It is thus a feature of at least one embodiment of the invention to accurately model uptake and clearing time differences among tissue, particularly between treated and healthy-tissue, to provide the ability to make accurate trade-offs between tumor treatment and toxicity to healthy-tissue.

The invention may provide, in one embodiment, an augmenting radiation dose map for external-beam radiotherapy to augment a radiation dose in the first volume of interest when a desired treatment radiation dose-rate cannot be achieved under the condition that the radiation dose-rate in the second volume of interest is no greater than the toxicity limit.

It is thus a feature of at least one embodiment of the invention to promote a synergistic combination of external-beam radiotherapy and targeted radiopharmaceuticals by providing an improved model of radiopharmaceutical-induced radiation dose consistent with the accuracy provided by external-beam radiotherapy.

A library of toxicity limits for organs may be provided and the input volumes of interest may be organ names for the volumes of interest to automatically deduce the toxicity limits.

It is thus a feature of at least one embodiment of the invention to permit the treatment planner to identify volumes of interest as particular organs in order to provide for automatic optimization of delivery amount and delivery times for the radiopharmaceutical.

The system may determine the delivery amounts and delivery times by using a linear superposition of the active times of the imaging-radiopharmaceutical.

It is thus a feature of at least one embodiment of the invention to provide a highly versatile method of treatment planning for radiopharmaceuticals that allows a single imaging experiment to be used to construct a wide variety of different possible treatment plans.

The system may receive from a physician or other user a desired radiation dose map of the first volume of interest indicating the desired radiation dose in that volume of interest during a particular time. A cumulative radiation dose map of the first volume of interest may then be produced from the three-dimensional data set to compute a difference radiation dose therebetween for external radiation beam treatment.

It is thus a feature of at least one embodiment of the invention to address the problem of tumor hypoxia, or limited blood flow in some regions of a tumor, through the use of external-beam radiotherapy. The ability to treat the margins of the tumor with radiopharmaceuticals complements the ability of external-beam radiotherapy to treat a tumor center. The hypoxia introduces an increase oxygen enhancement ratio which has to be compensated for through increased radiation dose, thus combined therapies.

In one embodiment, the invention may compute an achievable external radiation beam radiation dose and iteratively correct the difference between radiation dose and the treatment schedule to provide a desired radiation dose to the first volume.

It is thus a feature of at least one embodiment of the invention to accommodate the physical limitations of external-beam radiotherapy by compensating with the radiopharmaceutical radiation dose and vice versa.

The imaging-radiopharmaceutical will typically be different from the treatment-radiopharmaceutical and accordingly the invention may include the step of correcting the active time schedule for the imaging-radiopharmaceutical to reflect an active time schedule of the treatment-radiopharmaceutical. This correction may change radiation dose-rate within the first and second volumes, for example reflecting different half-lives of different radionuclides, while preserving relative uptake between the first and second volumes.

It is thus a feature of at least one embodiment of the invention to permit imaging-radiopharmaceuticals to be used to develop precise models of the behavior of treatment-radiopharmaceuticals before the treatment-radiopharmaceuticals are used.

The imaging-radiopharmaceutical may be identical to the treatment-radiopharmaceutical with the exception of a radioactive isotope.

It is thus an object of the invention to test the same targeting mechanism that will be used with the treatment-radiopharmaceutical.

These particular features and advantages may apply to only some embodiments falling within the claims and thus do not define the scope of the invention.

DETAILED DESCRIPTION OF THE PREFERRED EMBODIMENT

Figure 1:
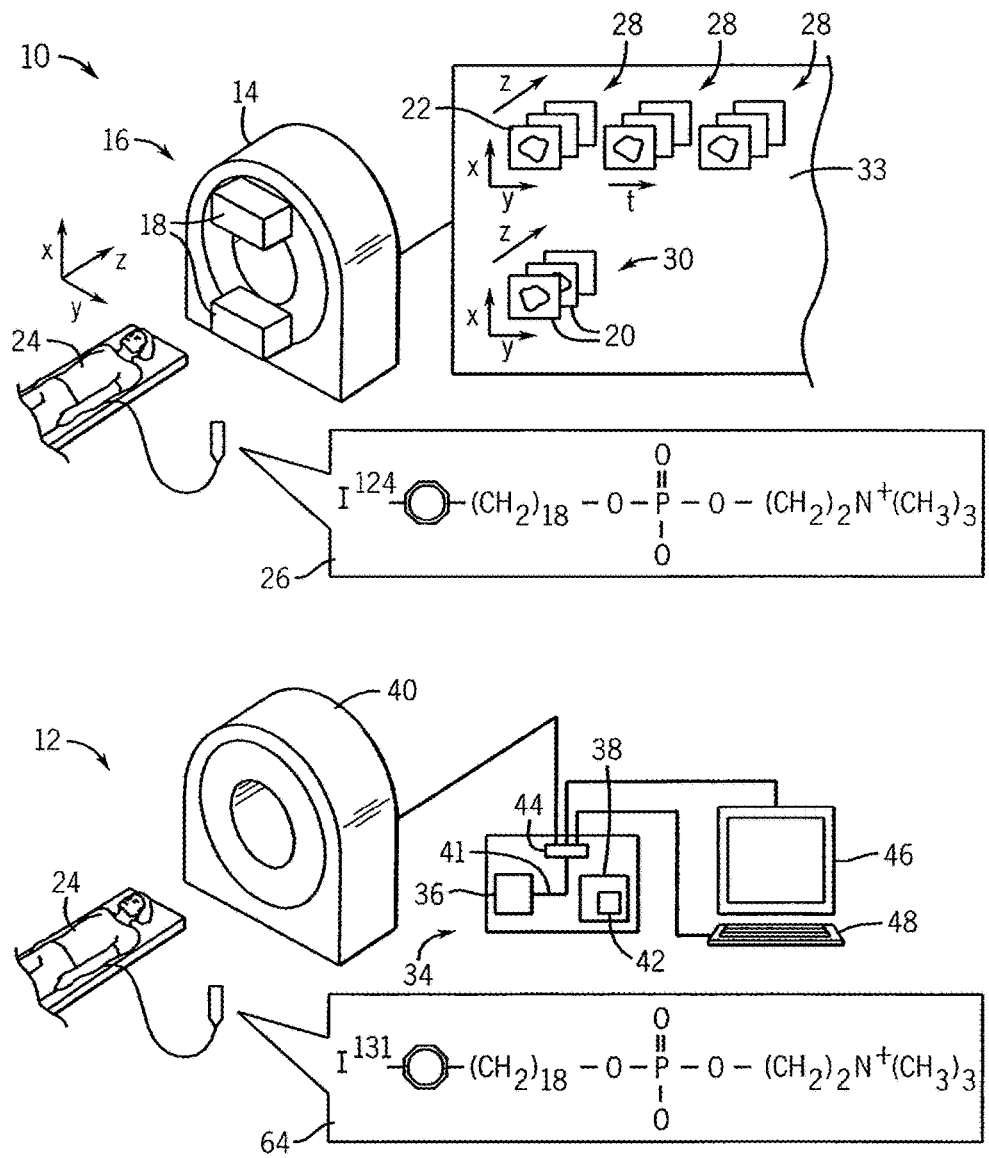
FIG. 1 is a schematic overview of the process implemented by the present invention.

Referring now to FIG. 1, the present invention provides a two-step process for the administration of a treatment-radiopharmaceutical having an imaging phase 10 followed by a treatment phase 12.

In one embodiment, the imaging phase 10 uses a combination SPECT/CT or PET/CT machine 14. Such a machine employs a conventional CT gantry 16 together with area gamma sensors 18 to provide a set of spatially aligned tomographic x-ray images 20 and corresponding tomographic emitted-radiation images 22 typically taken along a transverse ("x-y") cross-sectional plane through the patient 24. Tomographic x-ray images 20 and tomographic emitted-radiation images 22 displaced along the anterior-posterior ("z") axis complete a three-dimensional data scan used by the present invention producing a volumetric CT image set 30 and a volumetric emitted-radiation image set 28.

Contemporaneously with the CT scan, the patient 24 may be injected with a radiopharmaceutical 26, for example, NM404 tagged with an imaging radionuclide I124. A description of this radiopharmaceutical 26 is found in U.S. patent application 2005/0196339 entitled: "Phospholipid Analogs As Diapeutic Agents and Methods Thereof", published Sep. 8, 2005, naming the present inventor and hereby incorporated by reference. This particular radiopharmaceutical 26 emits gamma rays compatible with SPECT imaging.

As will be understood from the following discussion, the present invention is not limited to this particular radiopharmaceutical 26 or this particular radionuclide. Accordingly, the tomographic emitted-radiation images 22 may be collected using other radiopharmaceutical and with other imaging modalities, for example PET.

The collection of data of the volumetric emitted-radiation image set 28 continues for a period of time sufficient for the pharmacokinetic properties of the radiopharmaceutical 26 to be determined. Typically this period will be long enough for the radiopharmaceutical 26 to be taken up into the targeted tissue of the patient 24 and expelled from the body or to be exhausted by half-life decay. This time period will often span many days and, accordingly, the patient 24 may return to the hospital or clinic on a periodic basis for acquisition of each volumetric emitted-radiation image set 28. Periodically in this process, a new volumetric CT image set 30 may be obtained (or selected tomographic x-ray images 20) to, permit accurate alignment of the volumetric emitted-radiation image sets 28 with earlier and later data using the higher resolution CT data.

While the preferred embodiment employs x-ray CT data, it will be appreciated that other imaging modalities may be used in this capacity or that the volumetric emitted-radiation image set 28 may be used alone without a separate data set for alignment or volume definition as will be described below.

Figure 2:
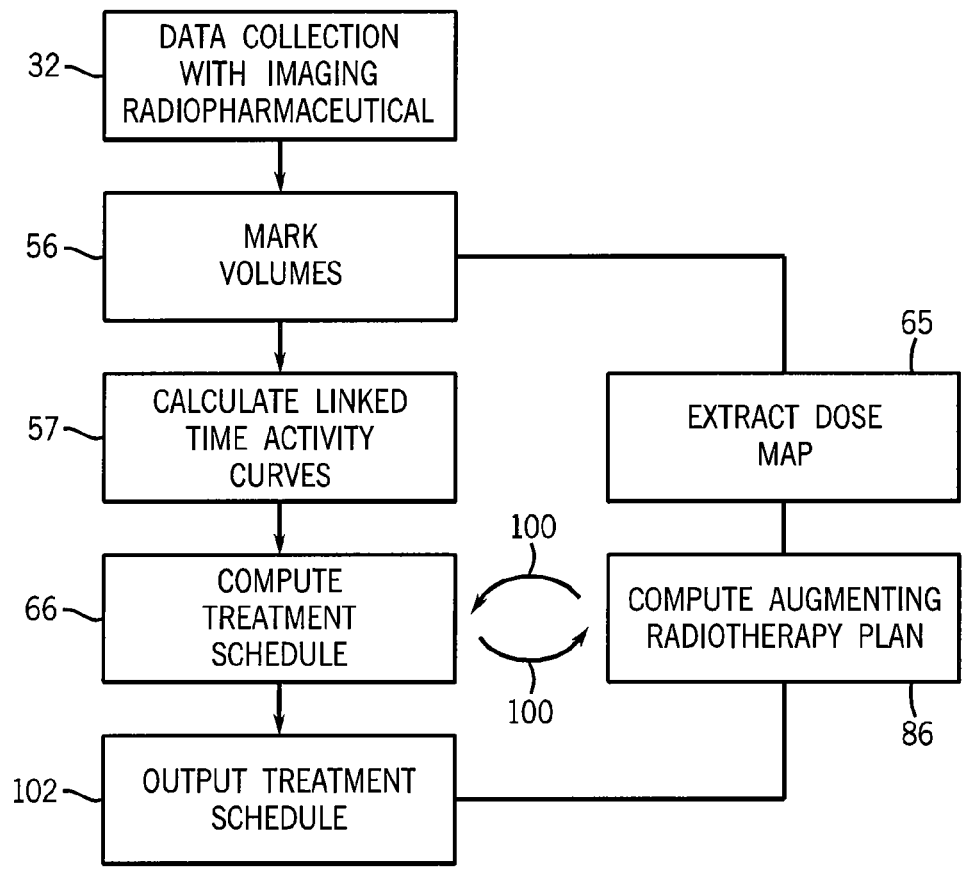
FIG. 2 is a flow chart of the steps of the present invention as may be implemented in whole or in part on one or more electronic computers.

At the conclusion of this process a model data set 33 will have been collected including multiple volumetric CT image sets 30 and multiple volumetric emitted-radiation image sets 28. Referring also to FIG. 2, when the model data set 33 has been collected, as indicated by process block 32, it may be loaded in a workstation 34, for example, a free standing personal computer or a workstation associated with the SPECT/CT machine 14 or (as shown) associated with an external-beam radiation therapy machine 40. The workstation 34 will preferably be of a type that can execute commercially available treatment planning software.

As is generally understood the art, such workstations 34 may include one or more processors 36 communicating with memory 38 by means of an internal bus 41. The memory 38 may hold a program 42 implementing one or more steps of the present invention as well as data libraries, as will be described. The bus 41 may communicate with an interface 44 providing for graphics display on monitor 46 and the entry of data through keyboard 48 or the like. The interface 44 may also provide data to the external-beam radiation therapy machine 40 or receive data (not depicted) from the SPECT/CT machine 14.

Figure 3:
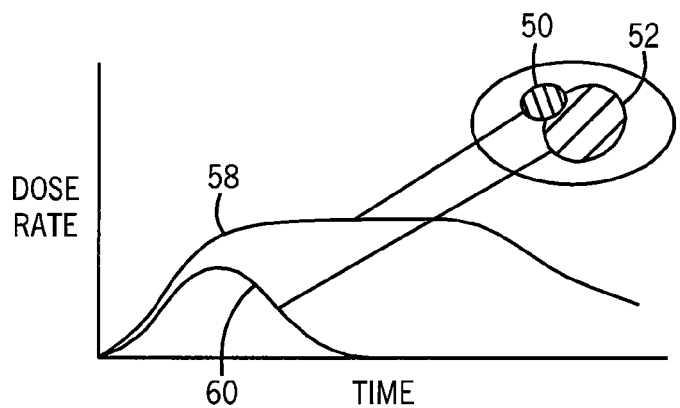
FIG. 3 is a graph showing a time activity curve collected using an imaging-radiopharmaceutical for two volumes of interest.

Referring now to FIGS. 2 and 3, the model data set 33 may be loaded into memory 38 and displayed using conventional techniques to allow volumes of interest (VOIs) within the tissue to be identified with respect to the CT images. For example, a first tumor volume of interest 50 (tumor VOI) and an adjacent healthy-tissue volume of interest 52 (healthy-tissue VOI) may be identified. This identification describes a three-dimensional volume and may be performed, for example, by the reviewing of successive tomographic x-ray images 20 of the patient and a drawing of an outline around the particular volumes of interest. This process establishes x-y boundaries for each tomographic x-ray image 20 and multiple x-y boundaries over different images along the z-axis established by the remaining dimension of the VOI. The marking of the volumes of interests will typically be with respect to the volumetric CT image set 30 but may be informed by the data of the volumetric emitted-radiation image set 28 as well or may use the volumetric emitted-radiation image set 28 alone.

Upon completion of the definition of the volumes of interest, as indicated by process block 56, the program may proceed to process block 57 where time activity curves are calculated for each of the volumes so identified. Time activity curves provide instantaneous radiation dose-rates as a function of time and the integral or area under the time activity curves provides total radiation dose.

This calculation process first segregates data elements of the volumetric emitted-radiation image set 28 to one of the volumes of interest 50 and 52 for each time period associated with the acquisition of the volumetric emitted-radiation image set 28. The emitted-radiation in each data element of a given volume of interest 50 and 52 for a particular time is then convolved with a radiation dose point kernel to define the dose-rate for that time period. Together, the dose-rates for the different time periods provide time activity curve 58 (tumor TAC) associated with tumor VOI 50 and healthy-tissue time activity curve 60 (healthy-tissue TAC) associated with healthy-tissue VOI 52. The radiation dose point kernel may be density corrected (using tissue density derived from the CT scan or the like). Other methods for determining dose rate may also be used including but not limited to a Monte Carlo dose calculation and similar techniques.

As depicted in FIG. 3, the healthy-tissue TAC 60 associated with tissue that is not targeted by the radiopharmaceutical 26 will generally exhibit lower uptake (indicated by the lower peak of the healthy-tissue TAC 60) and a shorter activity time (indicated by the shorter duration of the peak of healthy-tissue TAC 60). In contrast, the targeting effect of the radiopharmaceutical 26 with respect to the tumor cells in the tumor VOI 50 results in a higher peak for tumor TAC 58 and a far longer duration as the radiopharmaceutical 26 is held in the tissues.

Figure 5:
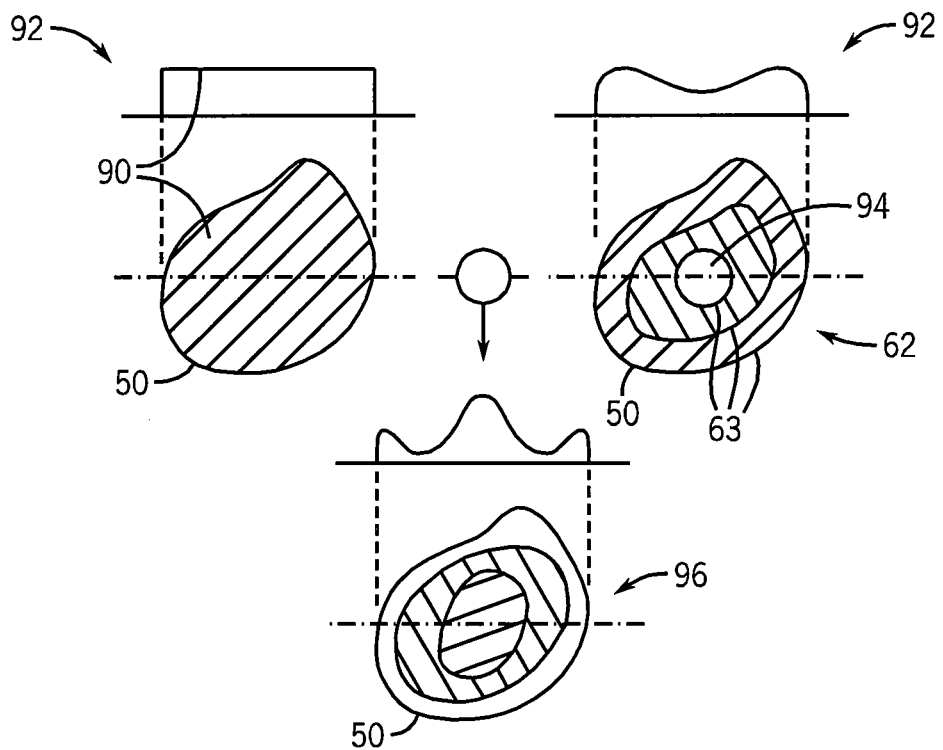
FIG. 5 is graphical representations of a desired radiation dose map and an actual radiation dose map produced by administration of the radiopharmaceutical, the difference providing a dose map for an augmenting external-beam radiation treatment plan.

Referring now momentarily to FIG. 5, as shown by process block 65, at the time of computation of the tumor TAC 58 and the healthy-tissue TAC 60, a radiation dose map 62 of tumor VOI 50 may be developed providing multiple iso-radiation dose lines 63 indicating the radiation dose received within the tumor VOI 50. This dose map 62 may be a single map obtained by integrating the total radiation dose of the tumor VOI 50 for each volume element of the data set 33 within the tumor VOI 50 for the entire time of the tumor TAC 58, or may be a set of dose maps associated with each volumetric emitted-radiation image set 28. The use of this dose map 62 will be described below.

Referring now again to FIG. 1, during the second treatment phase 12 of the present invention, the patient 24 will be injected with a treatment-radiopharmaceutical 64. In this example, the treatment-radiopharmaceutical 64 is an NM404 with the radionuclide I131 or I125 substituted for I124. As will be understood, the present invention is not limited to this particular treatment-radiopharmaceutical 64 or this particular radionuclide nor is it necessary that the radiopharmaceutical 64 be suitable for imaging.

Generally, the radionuclide used in the treatment-radiopharmaceutical 64 will have a longer half-life than that used with the imaging-radiopharmaceutical 26 however; the same tracer component may be used to provide comparable uptake mechanisms. The treatment-radiopharmaceutical 64 will be administered to the patient 24 in a treatment schedule providing for delivery amounts and delivery times of the treatment-radiopharmaceutical 64 as computed by the present invention per process block 66 of FIG. 2.

Figure 4:
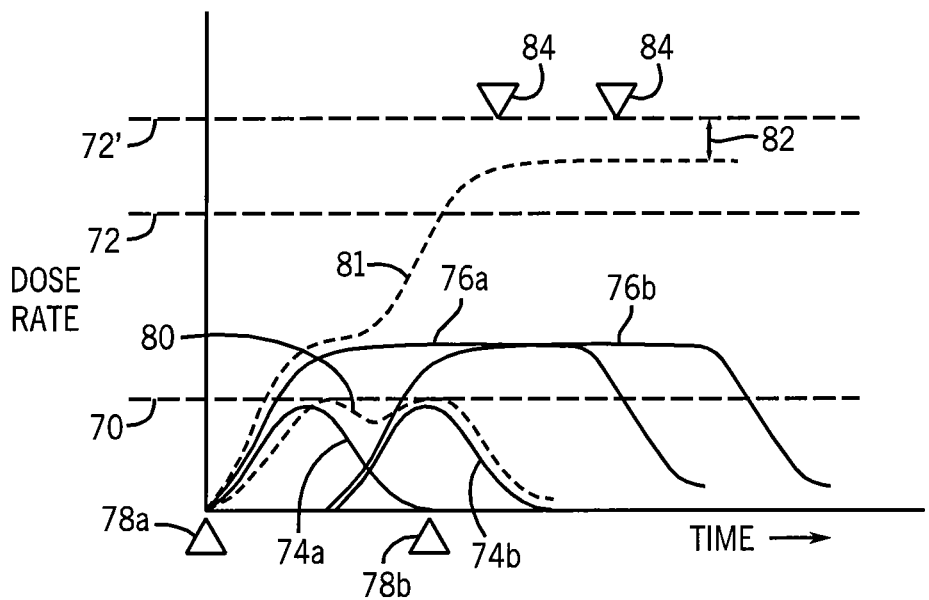
FIG. 4 is a graph showing development of a treatment plan for a treatment-radiopharmaceutical using the time activity curves of FIG. 3 as model elements.

Referring now to FIG. 4, the treatment schedule may be automatically calculated using a few setting parameters input by a clinician. The first parameter is a toxicity limit 70 for tissue in one or more healthy-tissue VOIs 52. The toxicity limit 70 may be, for example, automatically provided from a stored library of toxicity limits associated with particular organs and the clinician may simply assign an organ name to each of the healthy-tissue VOIs 52. When multiple healthy-tissue VOIs 52 have been identified with toxicity limit 70, a treatment schedule will be calculated to keep the radiation dose-rate below the toxicity limit 70 of all of the healthy-tissue VOIs 52. Alternatively, the absorbed dose, being the integral of the TAC 58, may be kept below the toxicity limit 70 expressed as an absorbed dose.

The clinician may also enter a desired radiation dose-rate 72 for the tumor VOI 50. This desired radiation dose-rate is set to provide a given minimum dose rate necessary to kill the tumor cells. Additionally, the clinician may enter a dose duration time indicating the desired length of treatment.

The time activity curves, shown in FIG. 3, are now adjusted to account for the different radionuclide used in the imaging-radiopharmaceutical 26 versus the treatment-radiopharmaceutical 64 to provide a healthy-tissue model curve 74 and a tumor model curve 76, conforming generally in shape to the healthy-tissue TAC 60 and the tumor TAC 58 adjusted in scale and possibly duration. The healthy-tissue model curve 74 and a tumor model curve 76 will be associated with a normalized treatment amount of the treatment-radiopharmaceutical 64 and can be simply scaled to accommodate different treatment quantities.

Using this principle, the healthy-tissue model curve 74a may be used to determine an administered quantity of the treatment-radiopharmaceutical 64 at a first radiopharmaceutical application 78a so that the peak of the healthy-tissue model curve 74a stays below the toxicity limit 70 for that tissue.

A second radiopharmaceutical application 78b may then be timed so that the sum (linear superposition) of the healthy-tissue model curve 74b for the second radiopharmaceutical application 78b and the healthy-tissue model curve 74a, being healthy-tissue rate total 80, stay below the toxicity limit 70.

Using these administered quantities, a corresponding tumor tissue rate total 81 can be determined by summing tumor model curves 76a and 76b associated with the radiopharmaceutical applications 78a and 78b in a manner similar to that used to produce healthy-tissue rate total 80. As a result of the longer retention time of the treatment-radiopharmaceutical 64 in the tumor tissue of tumor VOI 50, the tumor tissue rate total 81 continues to climb during this time to exceed the desired radiation dose-rate 72 while the healthy-tissue rate total 80 is constrained below the toxicity limit 70. In this way, either manually or automatically, an optimized schedule of the times of radiopharmaceutical applications 78 and quantities of the treatment-radiopharmaceutical 64 administered at those times can be determined. This schedule pattern may be repeated to provide the necessary duration of treatment time defined by the time during which the tumor tissue rate total 81 exceeds desired radiation dose-rate 72.

Referring still to FIG. 4, in some cases the desired radiation dose-rate 72' may exceed a peak level of the tumor tissue rate total 81 obtainable in the tumor VOI 50 while observing the toxicity limit 70 in the healthy-tissue VOI 52. Accordingly, the present invention may calculate an augmenting dose that may be output to the external-beam radiation therapy machine 40 to provide an augmenting radiation dose to the tumor VOI 50 to correct for a shortfall 82 in the dose-rate in the tumor VOI 50. The modeling system of the present invention allows precision in definition of the dose rate in particular volumes of interest 50 and 52 consistent with performing this type of augmentation by external-beam radiation therapy machines 40. Normally external-beam radiotherapy and targeted radionuclide therapy have quite different dose rates and accordingly their doses are added by conversion of both to a common "biologically effective dose" (BED). BED effectively normalizes both of these processes into infinitesimally small fractions. As shown in FIG. 4, this fractionation of the external radiation beam may be implemented by applying a radiation beam at multiple fractionation times 84 using the external-beam radiation therapy machine 40.

Referring again to FIG. 2, the computation of an augmenting radiation therapy plan shown generally by process block 86 may also be used to address a lack of uniformity in the radiation dose to the tumor VOI 50 by the treatment-radiopharmaceutical 64. Referring again to FIG. 5, the user may enter a desired radiation dose 90 to be received by the tumor VOI 50 here shown as a constant value in a cross section 92 through the tumor VOI 50. As computed at process block 65, lack of vascularization of the tumor tissue in the tumor VOI 50 (tumor hypoxia) may cause a lower radiation dose in a central region 94 of the tumor shown in a representative cross-section 92'.

The process of providing information to the external-beam radiation therapy machine 40 for this augmenting treatment made employ a subtraction of the actual radiation dose of the tumor VOI 50 defined by iso-radiation dose lines 63 (adjusted to accommodate the change of radiopharmaceutical 64 from radiopharmaceutical 26) from the desired radiation dose 90 to produce a difference dose 96 which can provide a desired radiation dose pattern for conventional treatment planning software for the external-beam radiation therapy machine 40.

Referring again to FIG. 2, this process of augmentation of the action of the radiopharmaceuticals with an external radiation beam may be performed iteratively with the actual radiation dose produced by the external-beam radiation therapy machine 40 being modeled and added to the radiation dose described by the iso-radiation dose lines 63 computed at process block 65. A new difference dose 96 may then be computed and used to adjust either the treatment schedule for the radiopharmaceutical 64 or the dose provided by the external-beam radiotherapy machine 40 as indicated by iteration arrows 100.

At process block 102, an output is provided consisting of a set of delivery amounts and delivery times for the radiopharmaceutical 64 and scheduled times and dose patterns for external-beam radiation. It will be understood that other of treatment planning outputs may also be provided including an indication of total dose and other graphic elements depicting the treatment planning process of the present invention including for example an estimated total dose or time activity curves for the treatment radiopharmaceutical 62 in each region of interest.

It will be appreciated that the present invention permits implementation of radiobiological monitoring, for example, using the Linear Quadratic Model and the determination of biological effective doses (BED). By incorporating the Lea-Catcheside factor into the biological effective dose equation, it is possible to set the desired radiation dose-rate 72 to include the radiobiological effects of radiation dose-rate and sub-lethal repair of both early and late responding tissues.

It is specifically intended that the present invention not be limited to the embodiments and illustrations contained herein, but include modified forms of those embodiments including portions of the embodiments and combinations of elements of different embodiments as come within the scope of the following claims.

We claim:

1. A system for planning a treatment schedule for a treatment-radiopharmaceutical, the system comprising:
   a radiation imaging machine adapted to scan a patient over a volume to measure emitted radiation;
   an electronic computer communicating with the radiation imaging machine and executing a stored program held in non-transitory computer readable medium to:
   (1) receive a three-dimensional data set from the radiation imaging machine indicating a history of tissue uptake of an imaging-radiopharmaceutical in at least one volume of interest;
   (2) deduce an active time of the imaging-radiopharmaceutical in the volume of interest, the active time in the form of a measured time activity curve providing radiation dose rate as a function of time over a treatment period for the at least one volume of interest; and
   (3) prepare a treatment schedule for a treatment-radiopharmaceutical different from the imaging-pharmaceutical, based on the active time of the imaging-radiopharmaceutical, the treatment schedule providing a schedule of multiple delivery amounts and delivery times for the treatment-radiopharmaceutical, the treatment schedule setting the multiple delivery amounts and delivery times according to a combining of multiple overlapping values of multiple time activity curves spanning the treatment schedule, the multiple time activity curves each based on the measured time activity curve, each of the multiple time activity curves referenced to one of the delivery amounts and delivery times, the delivery amounts and delivery times constrained by a requirement that an overlapping radiation dose rate from a combination of the multiple time activity curves referenced to the delivery amounts and delivery times remains above a desired radiation dose rate necessary to kill tumor cells based on the active time of the treatment-radiopharmaceutical deduced from the active time of the imaging radiopharmaceutical.

2. The system of claim 1 wherein the program receives a desired treatment radiation dose-rate and the treatment schedule determines radiation dose and delivery time to provide the desired treatment radiation dose-rate in the volume of interest.

3. The system of claim 2 wherein the program deduces an active time of the imaging-radiopharmaceutical in at least two volumes of interest and wherein the desired treatment radiation dose-rate is received for a first volume of interest and the program further receives a toxicity limit for a second volume of interest and wherein the program determines radiation dose and delivery time to maximize a time period when the radiation dose-rate in the first volume of interest is no less than the desired treatment radiation dose-rate under a condition that the radiation dose-rate in the second volume of interest be no greater than the toxicity limit.

4. The system of claim 3 wherein the program provides an augmenting radiation dose map for external-beam radiotherapy to augment a radiation dose in the first volume of interest when a desired treatment radiation dose-rate cannot be achieved under the condition that the radiation dose-rate in the second volume of interest be no greater than the toxicity limit.

5. The system of claim 3 further including a library of toxicity limits for organs and wherein the program accepts as inputs volumes of interest and organ names for the volumes of interest to automatically deduce toxicity limits for the input volumes of interest.

6. The system of claim 2 wherein the program further receives a desired radiation dose map of the first volume of interest and determines a radiation dose map of the first volume of interest from the three-dimensional data set to compute a difference radiation dose therebetween for augmenting external radiation beam treatment.

7. The system of claim 6 wherein the program further computes an achievable external radiation beam radiation dose and iteratively corrects the difference radiation dose and the treatment schedule to provide a desired radiation dose to the first volume of interest.

8. The system of claim 2 wherein the imaging-radiopharmaceutical is different from the treatment-radiopharmaceutical and including the step of correcting the active time for the imaging-radiopharmaceutical to reflect an active time of the treatment-radiopharmaceutical.

9. The system of claim 8 wherein the step of correcting changes absolute uptake within the first and second volumes of interest while preserving relative uptake between the first and second volumes.

10. The system of claim 1 wherein the program further outputs an image showing an expected radiation dose to the first volume of interest.

11. The system of claim 1 wherein the program determines the delivery amounts and delivery time by using a linear superposition of the active time of the imaging-radiopharmaceutical.

12. A method for planning a treatment schedule for a treatment-radiopharmaceutical comprising the steps of:
(a) collecting three-dimensional data on a radiation imaging machine related to emitted radiation from an imaging radiopharmaceutical;
(b) collecting from the three-dimensional data collected in step (a) on at least one electronic computer executing a stored program stored in non-transitory computer readable medium, a three-dimensional data set indicating a history of tissue uptake of the imaging-radiopharmaceutical in at least two volumes of interest;
(c) determining on at least one electronic computer executing a stored program stored in non-transitory computer readable medium, uptake of the imaging-radiopharmaceutical in the two volume of interest over a period of time, the determined uptakes being in the form of measured time activity curves providing radiation dose rates as a function of time over a treatment period for the at least two volumes of interest; and
(d) preparing on at least one electronic computer executing a stored program stored in non-transitory computer readable medium, a treatment schedule for a treatment-radiopharmaceutical different from the imaging-pharmaceutical, the schedule providing multiple delivery amounts and delivery times based on a combining of multiple overlapping values of multiple time activity curves spanning the treatment schedule, the multiple time activity curves each based on one of the measured time activity curves, each of the multiple time activity curves referenced to different of the delivery amounts and delivery times; the delivery amounts and delivery times of the treatment schedule selected to maximize an uptake in the first volume of interest above a desired radiation dose rate necessary to kill tumor cells from a combination of overlapping radiation dose rates of the multiple delivery amounts subject to controlling uptake in the second volume of interest during the schedule below a toxicity limit.

13. The method of claim 12 wherein the imaging-radiopharmaceutical is identical to the treatment-radiopharmaceutical with an exception of a radioactive isotope.

14. The method of claim 12 wherein the imaging and treatment-radiopharmaceutical are different radioisotopes attached to NM404.

15. The method of claim 12 wherein the three-dimensional data set is collected by an imaging machine selected from the group consisting of: a SPECT imager and a PET imager.

16. The method of claim 12 further including the step of calculating an augmenting radiation dose map for external-beam radiotherapy to augment a radiation dose in the first volume of interest when ,a desired treatment radiation dose-rate cannot be achieved under a condition that the radiation dose-rate in the second volume of interest be no greater than the toxicity limit.

17. The method of claim 12 further including the step of receiving a desired radiation dose for the first volume and calculating a radiation dose map of the first volume of interest from the three-dimensional data set to compute a difference radiation dose and using the different radiation dose to calculate an augmenting radiation dose map for external-beam radiotherapy.

18. The method of claim 17 wherein the program first computes an achievable external radiation beam radiation dose and iteratively corrects the difference radiation dose and the treatment schedule to provide a desired radiation dose to the first volume.

19. The method of claim 12 wherein the imaging-radiopharmaceutical is different from the treatment-radiopharmaceutical and including the step of correcting the active time schedule for the imaging-radiopharmaceutical to reflect an active time schedule of the treatment-radiopharmaceutical, and wherein the step of correcting changes absolute uptake within the first and second volumes while preserving relative uptake between the first and second volumes.

20. The method of claim 12 wherein the method further outputs an image showing an expected radiation dose to the first volume.

21. The method of claim 12 further including the step of injecting the treatment-radiopharmaceutical.

22. A system for planning a treatment schedule for a treatment-radiopharmaceutical, the system comprising:
- a radiation imaging machine adapted to scan a patient over a volume to measure emitted radiation;
- an external-beam radiation therapy machine;
- an electronic computer communicating with the radiation imaging machine and executing a stored program held in non-transitory computer readable medium to:
  (1) receive a three-dimensional data set from the radiation imaging machine indicating a history of tissue uptake of an imaging-radiopharmaceutical in at least one volume of interest;
  (2) deduce an active time of the imaging-radiopharmaceutical in the volume of interest, the active time in the form of a measured time activity curve providing radiation dose rate as a function of time over a treatment period for the at least one volume of interest;
  (3) prepare a treatment schedule for a treatment-radiopharmaceutical different from the imaging-pharmaceutical, based on the active time of the imaging-radiopharmaceutical, the treatment schedule providing a schedule of multiple delivery amounts and delivery times for the treatment-radiopharmaceutical, the treatment schedule setting the multiple delivery amounts and delivery times according to a combining of multiple overlapping values of multiple time activity curves spanning the treatment schedule, the multiple time activity curves each based on the measured time activity curve, each of the multiple time activity curves referenced to one of the delivery amounts and delivery times, the delivery amounts and delivery times constrained by a requirement that an overlapping radiation dose rate from a combination of the multiple time activity curves referenced to the delivery amounts and delivery times remains above a desired radiation dose rate necessary to kill tumor cells based on the active time of the treatment-radiopharmaceutical deduced from the active time of the imaging radiopharmaceutical; and
  (4) receive a desired radiation dose map of the volume of interest and determine a radiation dose map of the volume of interest from the three-dimensional data set to compute a difference radiation dose therebetween to provide to the external-beam radiation therapy machine.

* * * * *

UNITED STATES PATENT AND TRADEMARK OFFICE
CERTIFICATE OF CORRECTION

PATENT NO. : 10,007,961 B2
APPLICATION NO. : 12/556323
DATED : June 26, 2018
INVENTOR(S) : Grudzinski et al.

Page 1 of 1

It is certified that error appears in the above-identified patent and that said Letters Patent is hereby corrected as shown below:

In the Claims

Claim 16, Column 10, Line 60, replace ",a" with "a".

Signed and Sealed this
Twenty-first Day of August, 2018

Andrei Iancu
*Director of the United States Patent and Trademark Office*